(12) United States Patent
Collina et al.

(10) Patent No.: US 8,283,425 B2
(45) Date of Patent: Oct. 9, 2012

(54) MAGNESIUM DICHLORIDE-ETHANOL ADDUCTS AND CATALYST COMPONENTS OBTAINED THEREFROM

(75) Inventors: Gianni Collina, Ferrara (IT); Daniele Evangelisti, Ferrara (IT); Mario Sacchetti, Ferrara (IT)

(73) Assignee: Basell Poliolefine Italia s.r.l., Milan (IT)

( * ) Notice: Subject to any disclaimer, the term of this patent is extended or adjusted under 35 U.S.C. 154(b) by 747 days.

(21) Appl. No.: 10/584,004

(22) PCT Filed: Nov. 24, 2004

(86) PCT No.: PCT/EP2004/013371
§ 371 (c)(1),
(2), (4) Date: Aug. 1, 2008

(87) PCT Pub. No.: WO2005/063832
PCT Pub. Date: Jul. 14, 2005

(65) Prior Publication Data
US 2008/0293897 A1    Nov. 27, 2008

Related U.S. Application Data

(60) Provisional application No. 60/534,472, filed on Jan. 6, 2004.

(30) Foreign Application Priority Data

Dec. 23, 2003  (EP) .................................. 03104960

(51) Int. Cl.
*C08F 4/50*    (2006.01)

(52) U.S. Cl. ...................................................... 526/124.3
(58) Field of Classification Search ................ 526/124.3
See application file for complete search history.

(56) References Cited

U.S. PATENT DOCUMENTS

| | | | |
|---|---|---|---|
| 4,399,054 A | | 8/1983 | Ferraris et al. |
| 5,532,326 A | * | 7/1996 | Dall'Occo et al. ......... 526/125.7 |
| 6,417,132 B1 | | 7/2002 | Rong et al. |
| 2006/0025300 A1 | * | 2/2006 | Diego et al. .................. 502/115 |

FOREIGN PATENT DOCUMENTS

| | | |
|---|---|---|
| EP | 123767 | 11/1984 |
| EP | 395083 | 10/1990 |
| EP | 544340 | 6/1993 |
| WO | 98/44009 | 10/1998 |
| WO | 03/082930 | 10/2003 |
| WO | 2004/085495 | 10/2004 |

OTHER PUBLICATIONS

U.S. Appl. No. 10/537,079.*
U.S. Appl. No. 10/537,079, filed Jun. 1, 2005.*

* cited by examiner

*Primary Examiner* — Rebecca Anderson
*Assistant Examiner* — Sonya Wright
(74) *Attorney, Agent, or Firm* — Dilworth IP LLC

(57) ABSTRACT

Adducts are provided comprising $MgCl_2$, ethanol and a Lewis base (LB), said compounds being present in molar ratios defined by the following formula $MgCl_2 \cdot (EtOH)_n (LB)_p$ in which n is from 2 to 6 and p has values satisfying the following equation $p/(n+p) \leq 0.1$. The said adducts can be used as precursor in the preparation of high activity ZN catalysts.

6 Claims, No Drawings

MAGNESIUM DICHLORIDE-ETHANOL ADDUCTS AND CATALYST COMPONENTS OBTAINED THEREFROM

The present invention relates to magnesium dichloride/ethanol adducts which are characterized by particular chemical and physical properties. The adducts of the present invention are particularly useful as precursors of catalyst components for the polymerization of olefins.

$MgCl_2$.alcohol adducts and their use in the preparation of catalyst components for the polymerization of olefins are well known in the art.

Catalyst components for the polymerization of olefins, obtained by reacting $MgCl_2$.nEtOH adducts with halogenated transition metal compounds, are described in U.S. Pat. No. 4,399,054. The adducts are prepared by emulsifying the molten adduct in an immiscible dispersing medium and quenching the emulsion in a cooling fluid to collect the adduct in the form of spherical particles. No physical characterization regarding the degree of cristallinity of the adducts are reported.

In WO98/44009 are disclosed $MgCl_2$.alcohol adducts having improved characteristics and characterized by a particular X-ray diffraction spectrum, in which, in the range of 2θ diffraction angles between 5° and 15°, the three main diffraction lines are present at diffraction angles 2θ of 8.8±0.2°, 9.4±0.2° and 9.8±0.2°, the most intense diffraction lines being the one at 2θ=8.8±0.2°, the intensity of the other two diffraction lines being at least 0.2 times the intensity of the most intense diffraction line. Said adducts can be of formula $MgCl_2$.mEtOH.n$H_2O$
where m is between 2.2 and 3.8 and n is between 0.01 and 0.6. In addition to the above described X-ray spectrum, the above described adducts are characterized by a Differential Scanning Calorimetry (DSC) profile in which no peaks are present at temperatures below 90° C. or, even if peaks are present below said temperature, the fusion enthalpy associated with said peaks is less than 30% of the total fusion enthalpy.

These adducts are obtained by specific preparation methods involving the reaction between $MgCl_2$ and alcohol under conditions including long reaction times and absence of inert diluents or use of vaporized alcohol. Nothing is said, in the working examples, about the water content. The catalyst components obtained from these adducts have an increased activity over those obtained from the adducts of the prior art. However, the availability of catalyst components with still improved activity is always needed in view of the economic advantages obtainable in the operation of the industrial plants. In the international application WO03/082930 are described $MgCl_2$.mEtOH adducts in which m is from 2.5 to 3.2 optionally containing water up to a maximum of 1% wt based on the total weight of the adduct, characterized by a DSC profile in which the highest melting Temperature (Tm) peak is over 109° C. and has an associated fusion enthalpy (ΔH) of 103 J/g or lower. The catalyst components obtained from the adducts of the present invention are capable to give catalysts for the polymerization of olefins characterized by enhanced activity with respect to the catalysts prepared from the adducts of the prior art. Although the results are good, in order to obtain the desired adducts a strict control of the water in the system must be applied which can render the process too burdensome. In addition, the associated values of the fusion enthalpy may increase with the time due to the effect of the cristallization tendency and such a behaviour could lead to adducts that upon reaction with transition metal compounds can give catalyst components with somewhat worsened properties. It would be therefore important to find adducts capable to generate catalyst components having high polymerization activity and with a relatively low fusion enthalpy. Moreover, it would be useful if the increase of such relatively low fusion enthalpy would be at least delayed with the time in order to make easier the transformation in a catalyst component with valuable properties.

The present invention therefore relates to adducts comprising $MgCl_2$, ethanol and a Lewis base (LB) different from water, said compounds being present in molar ratios defined by the following formula $MgCl_2.(EtOH)_n(LB)_p$ in which n is from 2 to 6 and p has values satisfying the following equation $p/(n+p) \leq 0.1$.

Preferably, p has values satisfying the following equation $p/(n+p) \leq 0.05$, more preferably $p/(n+p) \leq 0.0125$.

The Lewis base can be selected from carboxylic acids, amides, aldehydes, esters, ethers, esters, ketones, silanes, amines, alcohol and nitriles. Preferably, the Lewis base is selected from ethers, esters, and compounds of formula $RX_m$ where R is a hydrocarbon group having from 1 to 20 carbon atoms, X is a —$NH_2$, a —NHR or —OH group and m is 1 or higher.

R is preferably an alkyl or alkiliden group having from 1 to 10 carbon atoms preferably from 2 to 6 carbon atoms, X is preferably —OH and m ranges from 1 to 6, and preferably is 1, 2 or 3. Preferred ethers are the C2-C20 aliphatic ethers and in particulars cyclic ethers preferably having 3-5 carbon atoms such as tetrahydrofurane, dioxane. Also suitable are the linear or cyclic aliphatic ethers having two or more ether groups. Preferred esters are the alkyl esters of C1-C10 aliphatic carboxylic acids and in particulars C1-C4 alkyl esters of aliphatic mono carboxylic acids such as ethylacetate and methyl formiate.

Representative examples of compounds of formula $RX_m$ are methanol, propanol, isopropanol, n-butanol, i-butanol, sec-butanol, tert-butanol, pentanol, 2-methyl-1-pentanol, 2-ethyl-1-hexanol, phenol, 4-methyl-1-phenol, 2,6-dimethyl-1-phenol, cyclohexanol, cyclopentanol, ethylene glycol, propylen glycol, 1,4-butanediol, glycerine, mannitol, polyvinyl-alcohol, acetonitrile, ethylenediammine, 3-picoline, triethanolammine, triethylammine, diisopropylammine.

Representative examples of the other Lewis Basis are acetic acids, acetonitrile formic aldehyde acetamide, formamide.

Generally, the fusion enthalpy associated to the said adducts is lower than 100 J/g and most preferably in the range 85-95 J/g. As mentioned above, these values are referred to the adducts prepared not earlier than 2 days from the date of measurement. However, the applicant has noticed that the adducts of the invention have a lower tendency of the fusion enthalpy to increase with the time. For example the increase can be none or limited to only 2-4 J/g after a week.

Water may be present in these adducts. Its content can be lower than 0.8% wt and preferably lower than 0.6% wt based on the sum of $MgCl_2$, ethanol and LB.

Particularly interesting are the adducts showing, in the DSC profile, only one peak, however, additional peaks in the 95-98° C. region may be present. In the latter case however, the fusion enthalpy associated to them is lower than 30% of the total fusion enthalpy, preferably lower than 20 and more preferably lower than 10%. The DSC analysis is carried out using the apparatus and the methodology described hereinafter.

It is possible, but not strictly required, that also the adduct of the present invention are characterized by an X-ray diffraction spectrum in which, in the range of 2θ diffraction angles between 5° and 15°, the three main diffraction lines are present at diffraction angles 2θ of 8.8±0.2°, 9.4±0.2° and 9.8±0.2°, the most intense diffraction lines being the one at 2θ=8.8±0.2°, the intensity of the other two diffraction lines being at least 0.2 times the intensity of the most intense diffraction line.

The adducts of the present invention can be prepared according to several methods. In particular the general methods described in WO98/44009 are suitable. One of the ways to reduce the water content is to carefully control the water content of the starting reactants. Both $MgCl_2$ and EtOH are in fact highly hygroscopic and tend to incorporate water in their structure. As a result, if the water content of the reactants is relatively high, the final $MgCl_2$-EtOH adducts may contain too high water content even if water has not been added as a separate component. Means for controlling or lowering the water content in solids or fluids are well known in the art. The water content in $MgCl_2$ can be for example lowered by drying it in an oven at high temperatures or by reacting it with a compound which is reactive towards water. As an example, a stream of HCl can be used to remove water from $MgCl_2$. Water from the fluids can be removed by various techniques such as distillation or by allowing the fluids to become in contact with substances capable to subtract water such as molecular sieves. Once these precautions have been taken, the reaction between the magnesium chloride and ethanol to produce the adducts of the invention can be carried out according to various methods.

According to one of these methods the adducts are prepared by dispersing the particles of magnesium dichloride in an inert liquid immiscible with and chemically inert to the molten adduct, heating the system at temperature equal to or higher than the melting temperature of $MgCl_2$.ethanol adduct and then adding the desired amount of alcohol in vapour phase. Depending on their physical properties, the LB can be added either with the $MgCl_2$ or with the EtOH in gas phase. The temperature is kept at values such that the adduct is completely melted.

The molten adduct is then emulsified in a liquid medium which is immiscible with and chemically inert to it and then quenched by contacting the adduct with an inert cooling liquid, thereby obtaining the solidification of the adduct.

The liquid in which the $MgCl_2$ is dispersed can be any liquid immiscible with and chemically inert to the molten adduct. For example, aliphatic, aromatic or cycloaliphatic hydrocarbons can be used as well as silicone oils. Aliphatic hydrocarbons such as vaseline oil are particularly preferred. After the $MgCl_2$ particles are dispersed in the inert liquid, the mixture is heated at temperatures preferably higher than 125° C. and more preferably at temperatures higher than 150° C. Conveniently; the vaporized alcohol is added at a temperature equal to or lower than the temperature of the mixture.

According to another method, the adducts of the invention are prepared by contacting $MgCl_2$, the LB and ethanol in the absence of the inert liquid dispersant, heating the system at the melting temperature of the adduct or above, and maintaining said conditions so as to obtain a completely melted adduct. Said molten adduct is then emulsified in a liquid medium which is immiscible with and chemically inert to it and finally quenched by contacting the adduct with an inert cooling liquid thereby obtaining the solidification of the adduct. In particular, the adduct is preferably kept at a temperature equal to or higher than its melting temperature, under stirring conditions, for a time period equal to or greater than 10 hours, preferably from 10 to 150 hours, more preferably from 20 to 100 hours. Alternatively, in order to obtain the solidification of the adduct, a spray-cooling process of the molten adduct can be carried out. All these methods provide solid adducts having a spherical morphology, which are very suitable in the preparation of spherical catalyst components for the polymerization of olefins and in particular for the gas-phase polymerization process. In the working examples reported below the preparation of the adducts of the invention is described in detail particularly with reference to alcohols and glycols as LB. The said preparations however, have a general validity and can be successfully used to prepare the adducts containing other LB of the invention.

The catalyst components to be used in the polymerization of olefins comprise a transition metal compound of one of the groups IV to VI of the Periodic Table of Elements, supported on the adducts of the invention.

A method suitable for the preparation of said catalyst components, comprises the reaction between the adducts of the invention and the transition metal compound. Among transition metal compounds particularly preferred are titanium compounds of formula $Ti(OR)_nX_{y-n}$ in which n is comprised between 0 and y; y is the valence of titanium; X is halogen and R is an alkyl radical having 1-8 carbon atoms or a COR group. Among them, particularly preferred are titanium compounds having at least one Ti-halogen bond such as titanium tetrahalides or halogenalcoholates. Preferred specific titanium compounds are $TiCl_3$, $TiCl_4$, $Ti(OBu)_4$, $Ti(OBu)Cl_3$, $Ti(OBu)_2Cl_2$, $Ti(OBu)_3Cl$. Preferably the reaction is carried out by suspending the adduct in cold $TiCl_4$ (generally 0° C.); then the so obtained mixture is heated up to 80-130° C. and kept at this temperature for 0.5-2 hours. After that the excess of $TiCl_4$ is removed and the solid component is recovered. The treatment with $TiCl_4$ can be carried out one or more times.

The reaction between transition metal compound and the adduct can also be carried out in the presence of an electron donor compound (internal donor) in particular when the preparation of a stereospecific catalyst for the polymerization of olefins is to be prepared. Said electron donor compound can be selected from esters, ethers, amines, silanes and ketones. In particular, the alkyl and aryl esters of mono or polycarboxylic acids such as for example esters of benzoic, phthalic, malonic and succinic acid are preferred. Specific examples of such esters are n-butylphthalate, di-isobutylphthalate, di-n-octylphthalate, diethyl 2,2-diisopropylsuccinate, diethyl 2,2-dicyclohexyl-succinate, ethyl-benzoate and p-ethoxy ethyl-benzoate. Moreover, can be advantageously used also the 1,3 diethers of the formula:

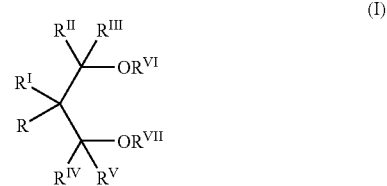

wherein R, $R^I$, $R^{II}$, $R^{III}$, $R^{IV}$ and $R^V$ equal or different to each other, are hydrogen or hydrocarbon radicals having from 1 to 18 carbon atoms, and $R^{VI}$ and $R^{VII}$, equal or different from each other, have the same meaning of R—$R^V$ except that they cannot be hydrogen; one or more of the R—$R^{VII}$ groups can be linked to form a cycle. The 1,3-diethers in which $R^{VI}$ and $R^{VII}$ are selected from $C_1$-$C_4$ alkyl radicals are particularly preferred.

The electron donor compound is generally present in molar ratio with respect to the magnesium comprised between 1:4 and 1:20.

Preferably, the particles of the solid catalyst components have substantially spherical morphology and an average diameter comprised between 5 and 150 μm. With the term substantial spherical morphology are meant those particles having a ratio between the greater and smaller axis equal to or lower than 1.5 and preferably lower than 1.3.

Before the reaction with the transition metal compound, the adducts of the present invention can also be subjected to a dealcoholation treatment aimed at lowering the alcohol content and increasing the porosity of the adduct itself. The dealcoholation can be carried out according to known methodologies such as those described in EP-A-395083. Depending on the extent of the dealcoholation treatment, partially dealcoholated adducts can be obtained having an alcohol content generally ranging from 0.1 to 2.6 moles of alcohol per mole of $MgCl_2$. After the dealcoholation treatment the adducts are reacted with the transition metal compound, according to the techniques described above, in order to obtain the solid catalyst components. The solid catalyst components according to the present invention show a surface area (by B.E.T. method) generally between 10 and 500 $m^2/g$ and preferably between 20 and 350 $m^2/g$, and a total porosity (by B.E.T. method) higher than 0.15 $cm^3/g$ preferably between 0.2 and 0.6 $cm^3/g$.

The catalyst components of the invention form catalysts for the polymerization of alpha-olefins $CH_2$=CHR, wherein R is hydrogen or a hydrocarbon radical having 1-12 carbon atoms, by reaction with Al-alkyl compounds. The alkyl-Al compound is preferably chosen among the trialkyl aluminum compounds such as for example triethylaluminum, triisobutylaluminum, tri-n-butylaluminum, tri-n-hexylaluminum, tri-n-octylaluminum. It is also possible to use alkylaluminum halides, alkylaluminum hydrides or alkylaluminum sesquichlorides such as $AlEt_2Cl$ and $Al_2Et_3Cl_3$ optionally in mixture with said trialkyl aluminum compounds.

The Al/Ti ratio is higher than 1 and is generally comprised between 20 and 800.

In the case of the stereoregular polymerization of α-olefins such as for example propylene and 1-butene, an electron donor compound (external donor) which can be the same or different from the compound used as internal donor can be used in the preparation of the catalysts disclosed above. In case the internal donor is an ester of a polycarboxylic acid, in particular a phthalate, the external donor is preferably selected from the silane compounds containing at least a Si—OR link, having the formula $R_a^1R_b^2Si(OR^3)_c$, where a and b are integer from 0 to 2, c is an integer from 1 to 3 and the sum (a+b+c) is 4; $R^1$, $R^2$, and $R^3$, are alkyl, cycloalkyl or aryl radicals with 1-18 carbon atoms. Particularly preferred are the silicon compounds in which a is 1, b is 1, c is 2, at least one of $R^1$ and $R^2$ is selected from branched alkyl, cycloalkyl or aryl groups with 3-10 carbon atoms and $R^3$ is a $C_1$-$C_{10}$ alkyl group, in particular methyl. Examples of such preferred silicon compounds are methylcyclohexyldimethoxysilane, diphenyldimethoxysilane, methyl-t-butyldimethoxysilane, dicyclopentyldimethoxysilane. Moreover, are also preferred the silicon compounds in which a is 0, c is 3, $R^2$ is a branched alkyl or cycloalkyl group and $R^3$ is methyl. Examples of such preferred silicon compounds are cyclohexyltrimethoxysilane, t-butyltrimethoxysilane and thexyltrimethoxysilane.

Also the 1,3 diethers having the previously described formula can be used as external donor. However, in the case 1,3-diethers are used as internal donors, the use of an external donor can be avoided, as the stereospecificity of the catalyst is already sufficiently high.

As previously indicated the components of the invention and catalysts obtained therefrom find applications in the processes for the (co)polymerization of olefins of formula $CH_2$=CHR in which R is hydrogen or a hydrocarbon radical having 1-12 carbon atoms.

The catalysts of the invention can be used in any of the olefin polymerization processes known in the art. They can be used for example in slurry polymerization using as diluent an inert hydrocarbon solvent or bulk polymerization using the liquid monomer (for example propylene) as a reaction medium. Moreover, they can also be used in the polymerization process carried out in gas-phase operating in one or more fluidized or mechanically agitated bed reactors.

The polymerization is generally carried out at temperature of from 20 to 120° C., preferably of from 40 to 80° C. when the polymerization is carried out in gas-phase the operating pressure is generally between 0.1 and 10 MPa, preferably between 1 and 5 MPa. In the bulk polymerization the operating pressure is generally between 1 and 6 MPa preferably between 1.5 and 4 MPa.

The catalysts of the invention are very useful for preparing a broad range of polyolefin products. Specific examples of the olefinic polymers which can be prepared are: high density ethylene polymers (HDPE, having a density higher than 0.940 g/cc), comprising ethylene homopolymers and copolymers of ethylene with alpha-olefins having 3-12 carbon atoms; linear low density polyethylenes (LLDPE, having a density lower than 0.940 g/cc) and very low density and ultra low density (VLDPE and ULDPE, having a density lower than 0.920 g/cc, to 0.880 g/cc) consisting of copolymers of ethylene with one or more alpha-olefins having from 3 to 12 carbon atoms, having a mole content of units derived from the ethylene higher than 80%; isotactic polypropylenes and crystalline copolymers of propylene and ethylene and/or other alpha-olefins having a content of units derived from propylene higher than 85% by weight; copolymers of propylene and 1-butene having a content of units derived from 1-butene comprised between 1 and 40% by weight; heterophasic copolymers comprising a crystalline polypropylene matrix and an amorphous phase comprising copolymers of propylene with ethylene and or other alpha-olefins.

The following examples are given to illustrate and not to limit the invention itself.

Characterization

The properties reported below have been determined according to the following methods: The DSC measurement were carried out with a PERKIN ELMER DSC 7 instrument at a scanning rate of 5° C./min in the range 5-125° C. Aluminum capsules having a volume of 40 μl filled with the samples in a dry-box were used in order to avoid hydration of the samples. The content of alcohol and other LB was determined via GC analysis.

EXAMPLES

General Procedure for the Preparation of the Catalyst Component

Into a 1 l steel reactor provided with stirrer, 800 $cm^3$ of $TiCl_4$ at 0° C. were introduced; at room temperature and whilst stirring 16 g of the adduct were introduced together with an amount of diisobutylphthalate as internal donor so as to give a donor/Mg molar ratio of 10. The whole was heated to 100° C. over 90 minutes and these conditions were maintained over 120 minutes. The stirring was stopped and after 30 minutes the liquid phase was separated from the sedimented solid maintaining the temperature at 100° C. A further treatment of the solid was carried out adding 750 $cm^3$ of $TiCl_4$ and heating the mixture at 120° C. over 10 min. and maintaining said conditions for 60 min under stirring conditions (500 rpm). The stirring was then discontinued and after 30 minutes the liquid phase was separated from the sedimented solid maintaining the temperature at 120° C. Thereafter, 3 washings with 500 cm³ of anhydrous hexane at 60° C. and 3 washings with 500 cm³ of anhydrous hexane at room temperature were carried out. The solid catalyst component obtained was then dried under vacuum in nitrogen environment at a temperature ranging from 40-45° C.

General Procedure for the Polymerization Test

A 4 liter steel autoclave equipped with a stirrer, pressure gauge, thermometer, catalyst feeding system, monomer feeding lines and thermostatting jacket, was used. The reactor was charged with 0.01 gr. of solid catalyst component 0.76 g of TEAL, 0.076 g of dicyclopentyldimetoxy silane, 3.2 l of propylene, and 1.5 l of hydrogen. The system was heated to 70° C. over 10 min. under stirring, and maintained under these conditions for 120 min. At the end of the polymerization, the polymer was recovered by removing any unreacted monomers and was dried under vacuum.

Example 1

In a vessel reactor equipped with a IKA RE 166 stirrer containing 136.63 g of anhydrous EtOH, and 0.93 g of butanol at room temperature were introduced under stirring 93.16 g of $MgCl_2$. Once the addition of $MgCl_2$ was completed, the temperature was raised up to 125° C. and kept at this value for 3 hours. After that, 1600 cm³ of OB55 vaseline oil were introduced and, while keeping the temperature at 125° C., the stirring was brought to 1500 rpm and kept at that value for two minutes. After that time the mixture was discharged into a vessel containing hexane which was kept under stirring and cooled so that the final temperature did not exceed 12° C. After 12 hours, the solid particles of the $MgCl_2.EtOH$ adduct recovered were then washed with hexane and dried at 40° C. under vacuum. The compositional analysis showed that they contained 54.2% by weight of EtOH and 0.3% wt of butanol.

The DSC profile showed a peak at 105.6° C., with an associated fusion enthalpy of 90.1 J/g. The catalyst component, prepared according to the general procedure, was tested according to the general polymerization procedure described above and gave the results reported in Table 1.

Example 2

The same procedure as in example 1 was carried out ($MgCl_2$ 92.64 g, ethanol 138.55 g) with the difference that the amount of butanol was increased to 2.77 g. The solid particles of the $MgCl_2.EtOH$ adduct recovered were then washed with hexane and dried at 40° C. under vacuum. The compositional analysis showed that they contained 51.1% by weight of EtOH and 0.7% of butanol.

The DSC profile showed a peak at 107.5° C., with an associated fusion enthalpy of 89.7 J/g. The catalyst component, prepared according to the general procedure, was tested according to the general polymerization procedure described above and gave the results reported in Table 1.

Example 3

The same procedure as in example 1 was carried out ($MgCl_2$ 86.0 g, ethanol 128.34 g) with the difference that 0.86 g of ethylenglycol were used instead of butanol. The solid particles of the $MgCl_2.EtOH$ adduct recovered were then washed with hexane and dried at 40° C. under vacuum. The compositional analysis showed that they contained 57.2% by weight of EtOH and 0.4% of glycol.

The DSC profile showed a peak at 107.4° C., with an associated fusion enthalpy of 90.1 J/g. The catalyst component, prepared according to the general procedure, was tested according to the general polymerization procedure described above and gave the results reported in Table 1

Comparison Example 1

The procedure of Example 1 was repeated with the difference that no butanol was used. The compositional analysis showed that the adduct contained 55.1% by weight of EtOH. The DSC profile showed a peak at 109° C., with an associated fusion enthalpy of 102 J/g. The catalyst component, prepared according to the general procedure, was tested according to the general polymerization procedure described above and gave the results reported in Table 1.

TABLE 1

| Example | Activity | I.I: | Poured bulk density |
|---------|----------|------|---------------------|
| 1       | 65.1     | 97.4 | 0.41                |
| 2       | 65       | 98.3 | 0.41                |
| 3       | 69.6     | 97.9 | 0.42                |
| Comp. 1 | 54       | 98.0 | 0.376               |

The invention claimed is:

1. A catalyst component for polymerizing at least one olefin comprising a product of a reaction between a transition metal compound and an adduct, wherein the transition metal compound is selected from a titanium compound of formula $Ti(OR)_nX_{y-n}$, wherein n is between 0 and y; y is a valence of titanium; X is halogen; and R is an alkyl radical comprising 1-8 carbon atoms, or COR, wherein R is a hydrocarbon group comprising from 1 to 20 carbon atoms, and the adduct comprises $MgCl_2$, ethanol and a Lewis base (LB) different from water, said adduct further comprising a fusion enthalpy lower than 100 J/g, and formula $MgCl_2 \cdot (EtOH)_n(LB)_p$, wherein n is from 2 to 6 and p is $0<p/(n+p)\leq0.1$, where the Lewis base is selected from ethers, esters, compounds of formula $RX_m$, and combinations thereof, wherein $RX_m$ is selected from the group consisting of methanol, propanol, isopropanol, n-butanol, sec-butanol, tert-butanol, pentanol, 2-methyl-1-pentanol, 2-ethyl-1-hexanol, phenol, 4-methyl-1-phenol, 2,6-dimethyl-1-phenol, cyclohexanol, cyclopentanol, ethylene glycol, propylene glycol, 1,4-butanediol, glycerine, mannitol, polyvinyl-alcohol, acetonitrile, ethylenediamine, 3-picoline, triethanolamine, triethylamine, and diisopropylamine.

2. A catalyst component for polymerizing at least one olefin, the catalyst component comprising a product of a reaction between a transition metal compound and an adduct, the adduct comprising $MgCl_2$, ethanol and a Lewis base (LB) different from water, said adduct further comprising a fusion enthalpy lower than 100 J/g, and formula $MgCl_2.(EtOH)_n(LB)_p$, wherein n is from 2 to 6 and p is $0<p/(n+p)\leq0.1$, where the Lewis base is selected from ethers, esters, compounds of formula $RX_m$, and combinations thereof, wherein $RX_m$ is selected from the group consisting of methanol, propanol, isopropanol, n-butanol, sec-butanol, tert-butanol, pentanol, 2-methyl-1-pentanol, 2-ethyl-1-hexanol, phenol, 4-methyl-1-phenol, 2,6-dimethyl-1-phenol, cyclohexanol, cyclopentanol, ethylene glycol, propylene glycol, 1,4-butanediol, glycerine, mannitol, polyvinyl-alcohol, acetonitrile, ethylenediamine, 3-picoline, triethanolamine, triethylamine, and diisopropylamine, and the transition metal compound being selected from at least one titanium compound, wherein the titanium compound is selected from $TiCl_3$, $TiCl_4$, $Ti(OBu)_4$, $Ti(OBu)Cl_3$, $Ti(OBu)_2Cl_2$, and $Ti(OBu)_3Cl$.

3. The catalyst component according to claim 1, wherein the reaction between the transition metal compound and the adduct is carried out in presence of an electron donor compound.

4. The catalyst component according to claim 3, wherein the electron donor is selected from esters, ethers, amines, and ketones.

5. A catalyst for polymerizing at least one olefin comprising a product of a reaction between a catalyst component and an aluminum alkyl compound, the catalyst component comprising a product of a reaction between a transition metal compound and an adduct, the adduct comprising $MgCl_2$, ethanol and a Lewis base (LB) different from water, said adduct further comprising a fusion enthalpy lower than 100 J/g, and formula $MgCl_2 \cdot (EtOH)_n(LB)_p$, wherein n is from 2 to 6 and p is $0<p/(n+p)\leq 0.1$, where the Lewis base is selected from ethers, esters, compounds of formula $RX_m$, and combinations thereof, wherein $RX_m$ is selected from the group consisting of methanol, propanol, isopropanol, n-butanol, sec-butanol, tert-butanol, pentanol, 2-methyl-1-pentanol, 2-ethyl-1-hexanol, phenol, 4-methyl-1-phenol, 2,6-dimethyl-1-phenol, cyclohexanol, cyclopentanol, ethylene glycol, propylene glycol, 1,4-butanediol, glycerine, mannitol, polyvinyl-alcohol, acetonitrile, ethylenediamine, 3-picoline, triethanolamine, triethylamine, and diisopropylamine, and the transition metal compound being selected from at least one titanium compound, wherein the titanium compound is selected from $TiCl_3$, $TiCl_4$, $Ti(OBu)_4$, $Ti(OBu)Cl_3$, $Ti(OBu)_2Cl_2$, and $Ti(OBu)_3Cl$.

6. A process for polymerizing at least one olefin of formula $CH_2=CHR$, wherein R is hydrogen or a hydrocarbon radical comprising 1-12 carbon atoms, carried out in presence of the catalyst according to claim 5.

* * * * *